(12) United States Patent
Fortin et al.

(10) Patent No.: US 9,339,390 B2
(45) Date of Patent: May 17, 2016

(54) BASE PIECE ADJUSTABLE PRIOR TO ATTACHMENT AND EASILY INCORPORATED INTO A VERTEBRAL REPLACEMENT DEVICE

(75) Inventors: Frédéric Fortin, Pessac (FR); Stéphan Gaillard, Rueil Malmaison (FR); Johann Robin, Begles (FR); Brice Sennequier, Pessac (FR)

(73) Assignee: BioSpine Implants, Pessac (FR)

( * ) Notice: Subject to any disclaimer, the term of this patent is extended or adjusted under 35 U.S.C. 154(b) by 0 days.

(21) Appl. No.: 12/935,615

(22) PCT Filed: Apr. 1, 2009

(86) PCT No.: PCT/FR2009/000383
§ 371 (c)(1),
(2), (4) Date: May 25, 2011

(87) PCT Pub. No.: WO2009/141513
PCT Pub. Date: Nov. 26, 2009

(65) Prior Publication Data
US 2011/0224793 A1      Sep. 15, 2011

(30) Foreign Application Priority Data

Apr. 1, 2008 (FR) .................................... 08 01783

(51) Int. Cl.
*A61F 2/44* (2006.01)
*A61B 17/70* (2006.01)
*A61F 2/30* (2006.01)

(52) U.S. Cl.
CPC ............... *A61F 2/44* (2013.01); *A61B 17/7001* (2013.01); *A61F 2/30742* (2013.01);
(Continued)

(58) Field of Classification Search
CPC ......... A61F 2/44; A61F 2/4455; A61F 2/446; A61F 2/4465; A61F 2/447
USPC ..................... 606/247–249; 623/17.11–17.16
See application file for complete search history.

(56) References Cited

U.S. PATENT DOCUMENTS 6,156,037 A * 12/2000 LeHuec et al. ................ 606/247
6,508,818 B2 * 1/2003 Steiner et al. .................. 606/71
(Continued)

FOREIGN PATENT DOCUMENTS

EP      1470803 A1    10/2004
FR      2897770 A1     8/2007
(Continued)

*Primary Examiner* — Mary Hoffman
(74) *Attorney, Agent, or Firm* — Hodgson Russ LLP

(57) ABSTRACT

Adjustable base piece (1) that can be incorporated into a prosthesis replacing the corpus vertebrae and comprising—a plate (11) positioned in contact with an internal face of the adjacent corpus vertebrae; —a curved panel (12) that can be adjusted in multiple directions by virtue of a ball stem (120) housed in a head (111) of the plate (11) which allows it to adopt the optimal angle with respect to this fixed plate (11), so that the said curved panel (12), thanks to its possibilities of multi-axis adjustment, can press espousing the external shape of the corpus vertebrae adjacent to the prosthesis, —a clamping plug (13) which, once tightened, fixes the panel (12) to the plate (11) in the desired position, thus allowing this adjustable base piece (1) to be simultaneously in contact with an internal surface of the adjacent corpus vertebrae, thus giving this base piece, once attached to the corpus vertebrae, great bearing stability, with good adaptation to suit all shapes of vertebra encountered in real life.

6 Claims, 5 Drawing Sheets

Figure 1:
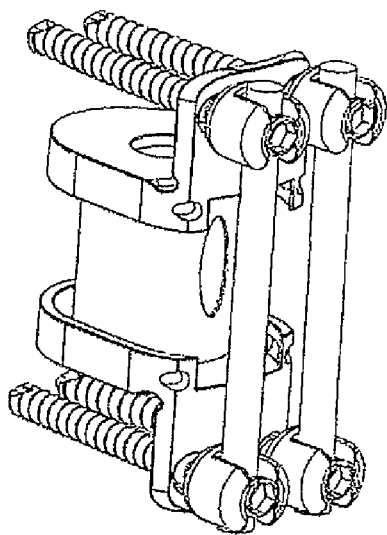

(52) U.S. Cl.
CPC .............. *A61F 2002/30235* (2013.01); *A61F 2002/30378* (2013.01); *A61F 2002/30507* (2013.01); *A61F 2002/30538* (2013.01); *A61F 2002/30578* (2013.01); *A61F 2002/30583* (2013.01); *A61F 2002/30604* (2013.01); *A61F 2002/30772* (2013.01); *A61F 2210/0085* (2013.01); *A61F 2220/0025* (2013.01); *A61F 2220/0033* (2013.01); *A61F 2230/0069* (2013.01); *A61F 2250/0006* (2013.01)

(56) References Cited

U.S. PATENT DOCUMENTS

| | | | |
|---|---|---|---|
| 7,172,627 B2 * | 2/2007 | Fiere et al. | 623/17.11 |
| 7,338,525 B2 * | 3/2008 | Ferree | 623/17.11 |
| 7,628,816 B2 * | 12/2009 | Magerl et al. | 623/17.16 |
| 8,216,312 B2 * | 7/2012 | Gray | 623/17.11 |
| 8,357,200 B2 * | 1/2013 | Adl | 623/17.14 |
| 8,454,694 B2 * | 6/2013 | Armstrong et al. | 623/17.11 |
| 8,496,708 B2 * | 7/2013 | Blain | 623/17.16 |
| 2001/0007072 A1 * | 7/2001 | Steiner et al. | 606/57 |
| 2004/0068318 A1 | 4/2004 | Coates et al. | |
| 2005/0101960 A1 * | 5/2005 | Fiere et al. | 606/72 |
| 2008/0161925 A1 * | 7/2008 | Brittan et al. | 623/17.16 |
| 2008/0183294 A1 * | 7/2008 | Adl | 623/17.16 |

FOREIGN PATENT DOCUMENTS

| | | |
|---|---|---|
| GB | 2364643 A | 2/2002 |
| WO | 99/65412 A1 | 12/1999 |
| WO | 20061113812 A2 | 10/2006 |

\* cited by examiner

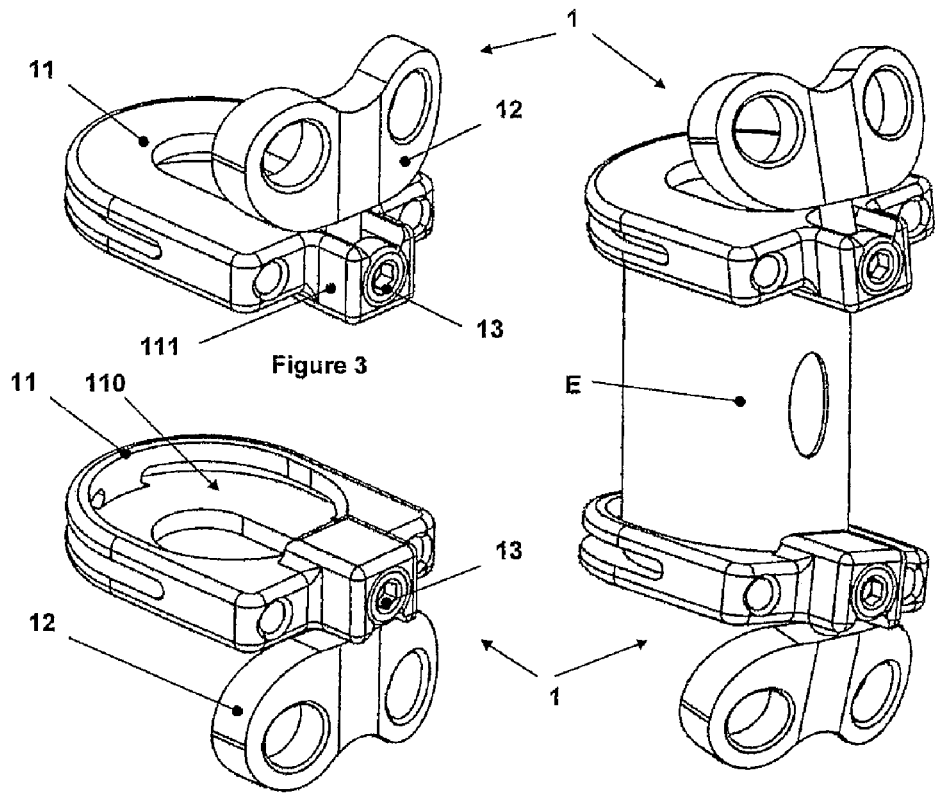
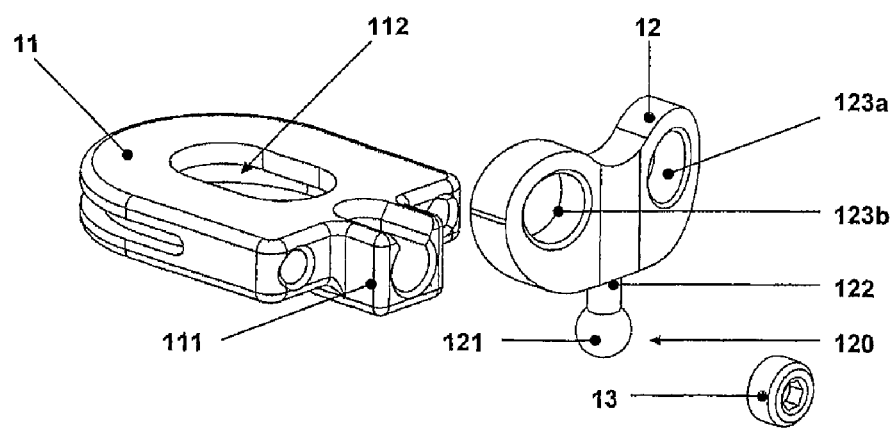

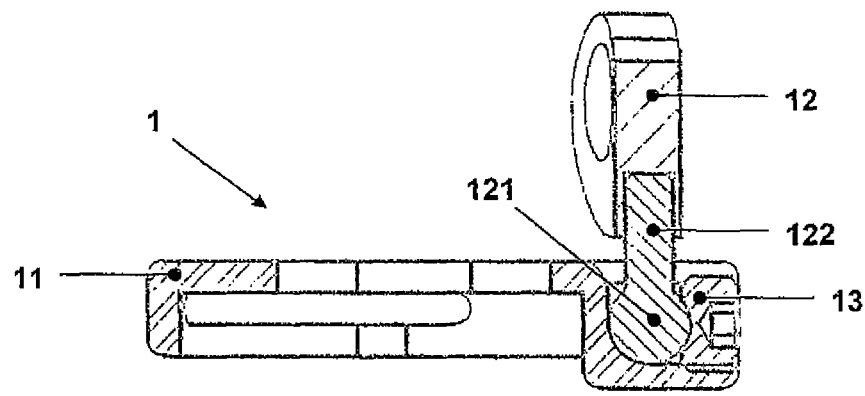
Figure 11
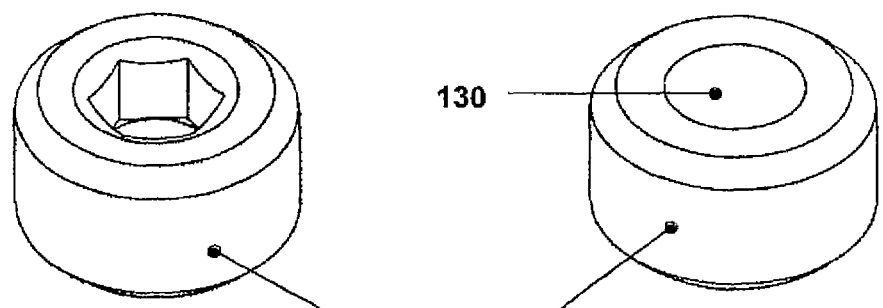
Figure 12
Figure 13
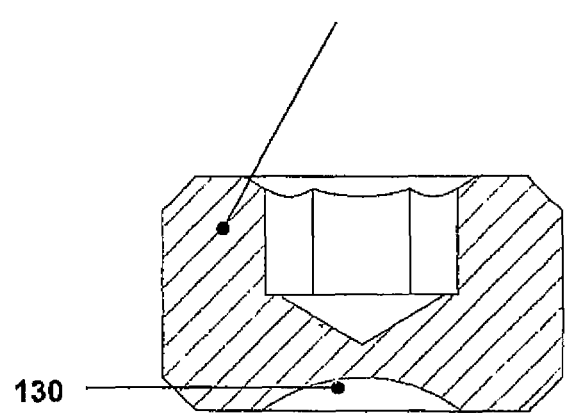
Figure 14

BASE PIECE ADJUSTABLE PRIOR TO ATTACHMENT AND EASILY INCORPORATED INTO A VERTEBRAL REPLACEMENT DEVICE

FIELD OF THE INVENTION

The present invention relates to an a collar that can be adjusted in order to be adapted to the shape of the vertebral body while thus being incorporated perfectly into a replacement device of a vertebral body having itself been the subject of inventions in the prior art.

In this prior art, the collars used were one-piece and included no adjustment; they had drawbacks associated with the fact that they lacked the possibilities of adjustment to the vertebrae. The operator therefore was obliged to make a compromise on the contact points of the prosthesis which led to assemblies resting partially on the adjacent vertebral bodies.

PRIOR ART

In a relatively old prior art, patent WO 99/65412 (PIONEER) describes a vertebral body furnished with two rigid collars connected by a single stem which is engaged in grooves which must be perfectly in line for installation. This case is an ideal configuration which occurs only very rarely in real life.

In a more recent prior art, the invention described in patent US 2004/0068318 (Bradley & Coates and others) also shows a prosthesis with two collars that are rigid but that were not designed to be installed on a vertebral body.

Similarly, patent EP 0974319 shows plenty of rigid collars that the operator tries to install in a vertebral body itself consisting of a multitude of rigid parts which have to be matched in order to be assembled and so that said collars remain correctly parallel, this being imposed by the assembly conditions. But it is in this case virtually impossible to make up for the vertebral misalignments. Moreover, when looking at the number of parts involved and their complexity, it is possible to have doubts about the mechanical integrity of such a device over time. The risks of breakage and of concentration of stresses are high and place in question the reliability of the prosthesis.

Finally, the patent called "Vertebral-body prosthesis that can be implanted by not very invasive surgery", a patent published under No. 2897770, describes and claims a bodily replacement device which comprises:

two collars made of biocompatible rigid material which closely conform to the shape of the vertebral body in the case of a suitable curvature, after ablation of the affected portion of the vertebral body.

four screws (two in the top portion and two in the bottom portion) which attach the rigid collars to the adjacent vertebral bodies two rigid stems made of biocompatible material, connecting said collars trapped in the split portions of the screw heads attached to the spinal column, these screw heads being immobilized by four tightening plugs, a flexible tubular casing, of which the shape of revolution is compatible with that of the rigid collars and of which the length is adjusted to the distance separating the collars, a filler cement, inserted in the liquid phase into the casing using a syringe through an orifice, which then hardens by polymerization.

The main functionalities provided by the combination of these means after assembly of the prosthesis are:

a good mechanical strength that is as firm as a healthy vertebra a very good distribution of the stresses on the adjacent vertebrae, this being due to the collars and to the cement injected and molded to the exact size of the cavity to be filled; this was already marked progress relative to the inventions prior to this invention published under No. FR2897770.

However, this invention obliged the operator to give preference to the surface in contact of the prosthesis with the adjacent vertebrae, notably because of the fixed angle of 90° of the collar. The operator had to carry out a precise surfacing of the bearing surfaces of each adjacent vertebra. The present invention avoids this drawback because the prostheses fitted with adjustable collars are perfectly adapted to the vertebrae by being pressed correctly onto the healthy surfaces of the bone of a single vertebra.

By being suitable for all profiles of vertebra, the new collar solves the stated problem by virtue of a fine adjustment that is possible on several axes. It is no longer necessary to carry out a minute preparation with it of the vertebral bone on which this collar presses.

The new adjustable collar can advantageously replace a known one-piece collar that comprises no adjustment, such as that described in the patented invention FR2897770.

Figure 2:
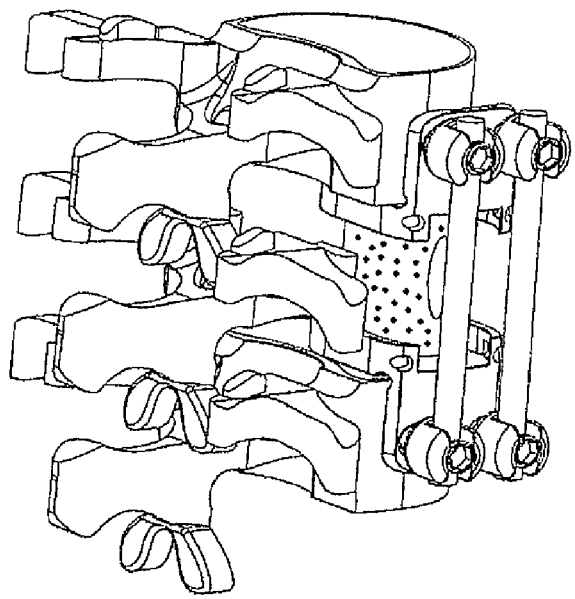
Figure 7:
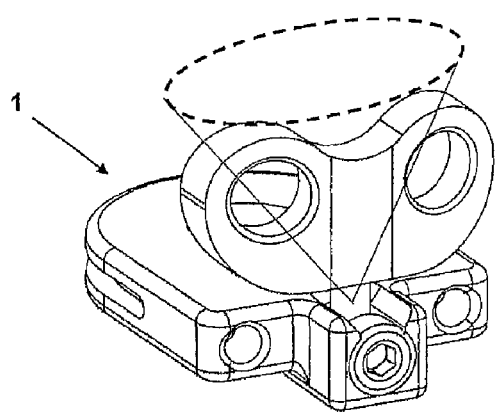
Figure 8:
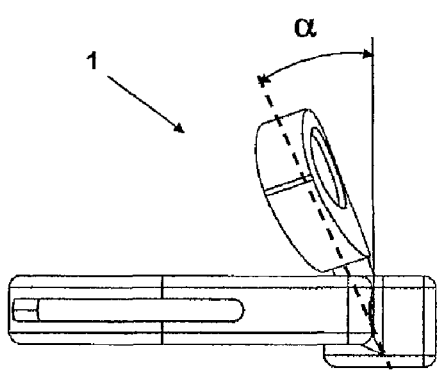
Figure 9:
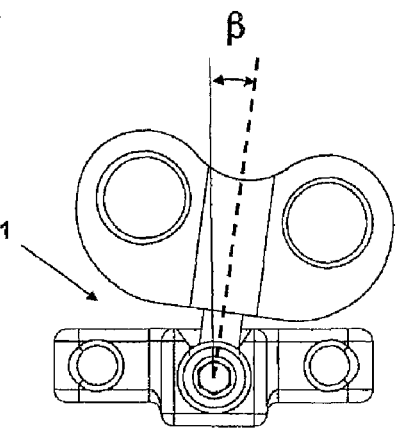
Figure 15:
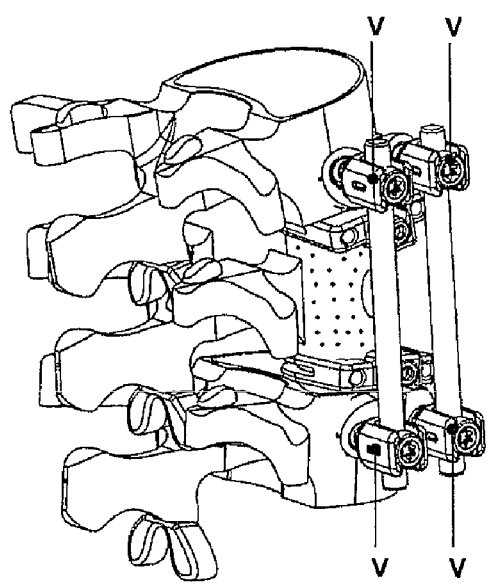
Figure 16:
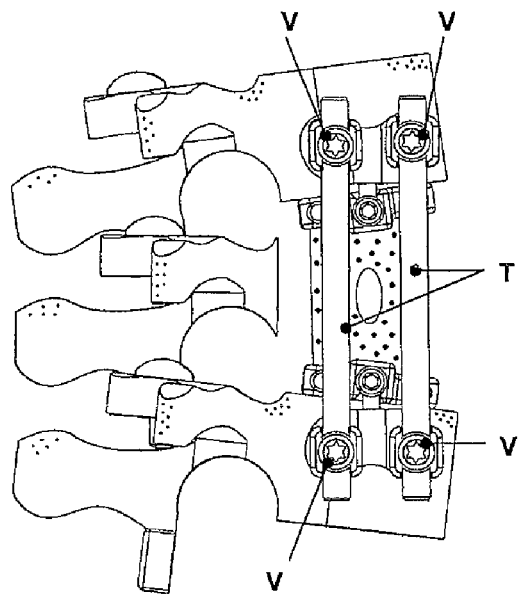
Figure 17:
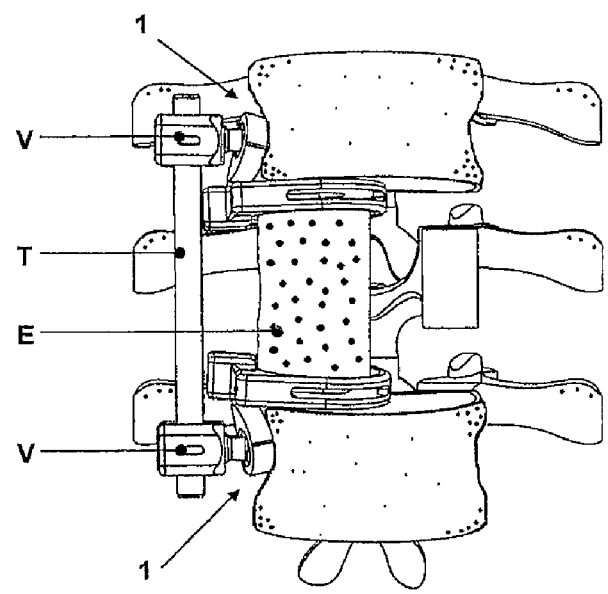

The figures used for understanding the invention are:

FIG. 1: plate 1/5, view in perspective of the prosthesis corresponding to the patented invention FR 2897770 (prior art), FIG. 2: plate 1/5, view of the prosthesis corresponding to the patented invention FR2897770 assembled with rigid collars onto a vertebral body (prior art), FIGS. 3 and 4, plate 2/5: views in perspective of the new adjustable collars positioned for the fitting of the flexible casing, FIG. 5, plate 2/5: a view in perspective of a casing fitted between two adjustable collars, FIG. 6, plate 2/5: exploded view in perspective of an adjustable collar, FIGS. 7, 8, 9 and 10, plate 3/5: views of the various possible positionings of an adjustable collar showing the acceptable angular ranges of movement that it can accept that may be independent or combined, FIG. 11, plate 4/5: a sectional view in profile of an adjustable collar which shows a swivel stem incorporated into the collar immobilized by a tightening plug, FIGS. 12, 13 and 14, plate 4/5: detailed views of a tightening plug of an adjustable collar, FIG. 15, plate 5/5: an isometric view of the prosthesis fitted with its adjustable collars mounted on the spinal column, FIG. 16, plate 5/5: a side view of the prosthesis fitted with its adjustable collars mounted on the spinal column with various orientations, FIG. 17, plate 5/5: an anterior view of the prosthesis fitted with its adjustable collars mounted on the spinal column with various orientations.

The adjustable collar 1 that is incorporated into a replacement prosthesis of the vertebral body comprises fixed means and adjustable means which make it possible to provide a correct attachment to the vertebral body (FIGS. 3, 4 and 6).

These means are as follows:

a fixed deck 11 that is positioned in contact with an inner face of the adjacent vertebral body, a curved plate 12 that can be adjusted on multiple axes by virtue of a swivel stem 120 that allows it to adopt the optimal angle relative to this fixed deck 11 so that said curved plate 12, by virtue of its multiaxial adjustment possibilities, can press while closely conforming to the outer shape of the vertebral body adjacent to the prosthesis, a tightening plug 13 which, once tightened, attaches the plate 12 to the deck 11 in the desired position, which allows this adjustable collar 1 to be simultaneously in contact with an inner surface of the adjacent vertebral body, thus conferring on this collar, once attached to the vertebral body, a great contact stability, with a good adaptation to all the shapes of vertebrae encountered in real life.

The deck 11 has:

on the inside: a recess 110 provided for the fitting of a flexible casing that can be cut in order to be adapted to a chosen length, which will contain an injectable cement hardening in a few minutes after its injection, at one of its ends: a head 111 in which the swivel stem 120 connected to the curved plate 12 is housed, formed of a sphere 121 (a swivel head) and of a stem 122 capable of turning inside the head 111.

The swivel stem 120 connected to the curved plate 12 is itself pierced with two holes 123a and b through which screws V pass for attaching this adjustable collar 1 to an outer surface of the vertebral body.

These screws V immobilize the curved plate 12 in contact with the outer surface of the vertebral body without causing superfluous movements of the deck 11 of the adjustable collar 1 when the tightening plug 13 is not yet tightened while the operator attaches the curved plate 12 with the screws V.

Figure 10:
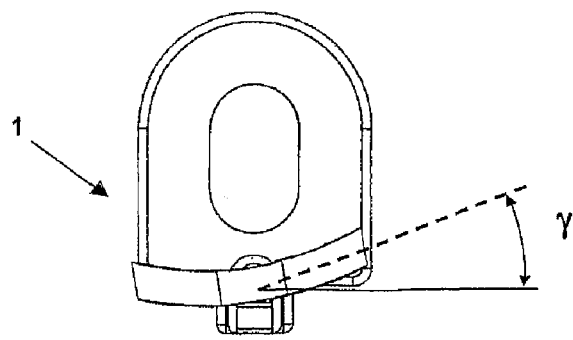

During this assembly, the swivel stem 120 (FIG. 6) connected to the curved adjustable plate 12 makes it possible, before tightening, to position the latter relative to the deck 11 with the following angular ranges of movement (FIGS. 7 to 10):

$$-20°<\alpha<+20°$$

$$-10°<\beta<+10°$$

$$0°<\gamma<360°$$

α corresponding to the possible angular range of movement in a profile vertical plane of the deck 11 (FIG. 8) forward/backward movements of the means 12

β corresponding to the possible angular range of movement in a rear vertical plane of the same deck 11 (FIG. 9) lateral movements of the means 12

γ corresponding to the rotation on itself of the curved plate 12 connected to the swivel about the axis of the swivel stem 120 (FIG. 10).

The deck 11 has an orifice 112 which promotes the formation of a bony bridge and improves the anchoring of the device to the vertebrae.

Before the plug 13 is tightened, the swivel stem 120 connected to the curved adjustable plate 12 is free, which makes it possible to position said curved plate 12.

The tightening of the plug 13 makes it possible to attach the deck 11 with the curved plate 12 in an optimal position of the collar obtained when the deck 11 and the curved plate 12 are in practically perfect contact on their respective vertebral face.

This tightening plug 13 has a concave recess 130 (FIGS. 13 and 14) the radius of which perfectly conforms to that of the sphere 121, the immobilization taking place by screwing of the plug 13 which then presses the swivel sphere 121 against the head 111, which makes it possible to attach the means 11 and 12.

Because of the novel means used and their functionalities, the adjustable collar 1 is perfectly positioned, which is never the case in the inventions of the prior art that do not have these adjustments.

FIGS. 15, 16 and 17 show the adjustable collar 1 inserted into a complete assembly of a device used as a prosthesis and attached to the vertebrae, corresponding to the invention (FR 2897770), but being much better adapted to the vertebral body.

Specifically, in the situation resolved by the present invention, it is seen that these adjustable collars 1 are perfectly adjusted to the vertebrae, by virtue of the presence of the angular ranges of movement (α,β,γ) connected to the swivel stem 121, which ranges of movement allow a precise adjustment of the adjustable collars 1 on the peripheral face and on the inner face of the vertebral body, features that are impossible to obtain with collars that are fixed and not adjustable.

These adjustable collars 1 make it possible to ensure in particular novel functionalities notably for the invention (FR 2897770) by being adapted to all the real geometries of vertebrae.

The final attachment of the adjustable collars 1 onto the vertebral body is obtained by screwing the screws V through the holes 123a and b, which gives an optimal solution of firmness to the assembly after tightening of the stems T connecting the two adjustable collars 1.

Finally, note that these novel adjustable collars 1 can also be used for other inventions.

The invention claimed is:

1. An adjustable collar for a replacement prosthesis of a vertebral body having an inner face and an outer shape, comprising:
   a fixed deck configured to be in contact with the inner face of the vertebral body, the fixed deck having a head;
   a curved plate having a swivel stem configured to be pivotably received in the head of the fixed deck such that the curved plate is pivotable relative to the fixed deck for conformance with the outer shape of the vertebral body; and
   a tightening plug configured to selectably cooperate with the head of the fixed deck to clamp the swivel stem in a fixed position thereby maintaining the fixed deck and curved plate in a desired position in contact with the vertebral body, and wherein the tightening plug does not pass through the swivel stem.

2. The adjustable collar of claim 1, wherein the fixed deck further comprises:
   a recess for fitting an adjustable length casing;
   wherein the plate further comprises two holes, each hole configured to receive a screw for attachment of the curved plate to the outer face of the vertebral body.

3. The adjustable collar of claim 1, wherein the swivel stem further comprises a stem and a swivel head at an end of the stem, the swivel head being shaped as a sphere and wherein the curved plate can swivel relative to the fixed deck between −20° and +20° on a sagittal plane, between −10° and +10° on a coronal plane, and between 0° and 360° about a longitudinal axis of the stem.

4. The adjustable collar of claim 1, wherein the tightening plug further comprises a concave recess having a shape that matches the spherical shape of the swivel head.

5. The adjustable collar of claim 2, wherein the swivel stem further comprises a stem and a swivel head at the end of the stem, the swivel head being shaped as a sphere and wherein the curved plate can swivel relative to the fixed deck between −20° and +20° on a sagittal plane, between −10° and +10° on a coronal plane, and between 0° and 360° about a longitudinal axis of the stem.

6. The adjustable collar of claim 2, wherein the tightening plug further comprises a concave recess having a shape that matches a spherical shape of the swivel head.

* * * * *